(12) United States Patent
Fritsch et al.

(10) Patent No.: US 8,434,184 B2
(45) Date of Patent: May 7, 2013

(54) FRACTURE RESISTANT BRUSH HEAD

(75) Inventors: Thomas Fritsch, Eppstein (DE); Ulrich Störkel, Bad Nauheim (DE)

(73) Assignee: Braun GmbH, Kronberg (DE)

(*) Notice: Subject to any disclaimer, the term of this patent is extended or adjusted under 35 U.S.C. 154(b) by 342 days.

(21) Appl. No.: 12/855,960

(22) Filed: Aug. 13, 2010

(65) Prior Publication Data

US 2012/0036656 A1 Feb. 16, 2012

(51) Int. Cl.
*A46B 13/00* (2006.01)

(52) U.S. Cl.
USPC ............... 15/22.2; 15/22.1; 15/167.1; 15/201

(58) Field of Classification Search .................... 15/22.1, 15/21.1, 21.2, 22.2, 23, 167.1, 167.2, 201
See application file for complete search history.

(56) References Cited

U.S. PATENT DOCUMENTS

| | | | |
|---|---|---|---|
| 5,077,855 A | 1/1992 | Ambasz | |
| 5,504,958 A | 4/1996 | Herzog | |
| 6,760,946 B2* | 7/2004 | DePuydt | 15/22.4 |
| 6,892,412 B2* | 5/2005 | Gatzemeyer et al. | 15/22.2 |
| 7,322,066 B2* | 1/2008 | Ping et al. | 15/22.1 |
| 7,356,866 B2* | 4/2008 | Chan | 15/22.1 |
| 7,761,947 B2* | 7/2010 | Blaustein et al. | 15/22.4 |
| 2007/0251033 A1* | 11/2007 | Brown et al. | 15/22.1 |
| 2009/0183324 A1 | 7/2009 | Fischer et al. | |

FOREIGN PATENT DOCUMENTS

| | | |
|---|---|---|
| DE | 35 44 256 A1 | 6/1987 |
| WO | WO 2008/040401 | 4/2008 |

* cited by examiner

*Primary Examiner* — Jeanette E. Chapman
(74) *Attorney, Agent, or Firm* — John P. Colbert (57) ABSTRACT

This application relates to electric toothbrushes and in particular to a brush section for an electric toothbrush. The brush section may include static contact elements and movable contact elements to perform a cleaning operation. A head portion of the brush section is resistant to fractures or other material damage which might result from impacts, such as for example caused by dropping the toothbrush. It is structured to transmit forces from the impact away from an interior region of the head portion, to pass through the side portions of the head portion.

13 Claims, 5 Drawing Sheets

FIGURE 3 though these are mere examples and are not intended to be limiting.

FRACTURE RESISTANT BRUSH HEAD

FIELD OF THE INVENTION

This application relates to electric toothbrushes and in particular to a brush section for an electric toothbrush.

BACKGROUND OF THE INVENTION

An electric toothbrush may incorporate a brush section that couples to a handle section. Mechanical linkages may connect one or more movable portions in the brush section to an electric drive disposed within an interior of the handle section. The electric drive may impart a rotary, oscillating or combined rotary oscillating motion to the movable portions so that they move in a rotary or oscillating manner. The movement of the movable portions provide a desired cleaning action.

Electric toothbrushes are often larger in size than non-electric toothbrushes, due to the presence of an electric motor, batteries, various mechanical linkages, electrically-driven head portions, and other components. Electric toothbrushes also often weigh more than non-electric toothbrushes, again due to the presence of those various components. In order to minimize the physical size and weight of an electric toothbrush, many of the individual components can be manufactured to be as small and light as practical. One of the factors limiting the use of small and light components in an electrical toothbrush, however, is durability. For example, it is desirable for a toothbrush to meet certain "drop test" requirements. In this context, a drop test specifies one or more laboratory conditions which are typically meant to emulate what would occur if a user were to drop the toothbrush. Such conditions include, for example, the height of a drop, the orientation of the toothbrush when it is dropped, the material and conditions of the surface impacted by the toothbrush to stop its fall, and the like. The toothbrush passes the drop test if, after being dropped under the specified conditions, it is not fractured or otherwise materially damaged. Thus, the choice of materials and degree of minimization to reduce the physical size and weight of a toothbrush is limited by durability requirements, such as drop test requirements.

The present application sets forth an electric toothbrush design which advantageously increases the resistance of the brush head to fractures or other material damage which might otherwise result from impacts, such as for example caused by dropping the toothbrush.

SUMMARY OF THE INVENTION

In one embodiment, a brush section for an electrical toothbrush housing an electric drive, the brush section having a head portion includes a frame including a first plurality of contact elements supported within the frame; a movable contact element holder including a second plurality of contact elements supported within the movable contact element holder; and an extension portion of the movable contact element holder arranged at a tip end of the head portion, with a gap disposed between the extension portion and the frame. The movable contact element holder being structured to receive a cleaning motion from the electric drive to have at least one freedom of motion relative to the first plurality of contact elements. And, at least a first portion of the gap in a side periphery region of the head portion is smaller in width than a second portion of the gap in an interior region of the toothbrush head.

In another embodiment, a brush section for an electrical toothbrush housing an electric drive, the brush section having a head portion includes a frame including a first plurality of contact elements supported within the frame; a movable contact element holder including a second plurality of contact elements supported within the movable contact element holder; an extension portion of the movable contact element holder arranged at a tip end of the head portion; and means for distributing an impact force away from an interior region of the head portion. The movable contact element holder being structured to receive a cleaning motion from the electric drive to have at least one freedom of motion relative to the first plurality of contact elements.

In another embodiment, a brush section for an electrical toothbrush housing an electric drive, the brush section having a head portion includes a frame including a first plurality of contact elements supported within the frame; a movable contact element holder including a second plurality of contact elements supported within the movable contact element holder; and an extension portion of the movable contact element holder arranged at a tip end of the head portion, with a gap disposed between the extension portion and the frame. The movable contact element holder being structured to receive a cleaning motion from the electric drive. And, the gap is configured such that the brush head portion is able to absorb at least about 1.3 Newtons of energy applied via a force D without fracture.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. None of the drawings is necessarily to scale.

DETAILED DESCRIPTION OF THE INVENTION

Figure 1:
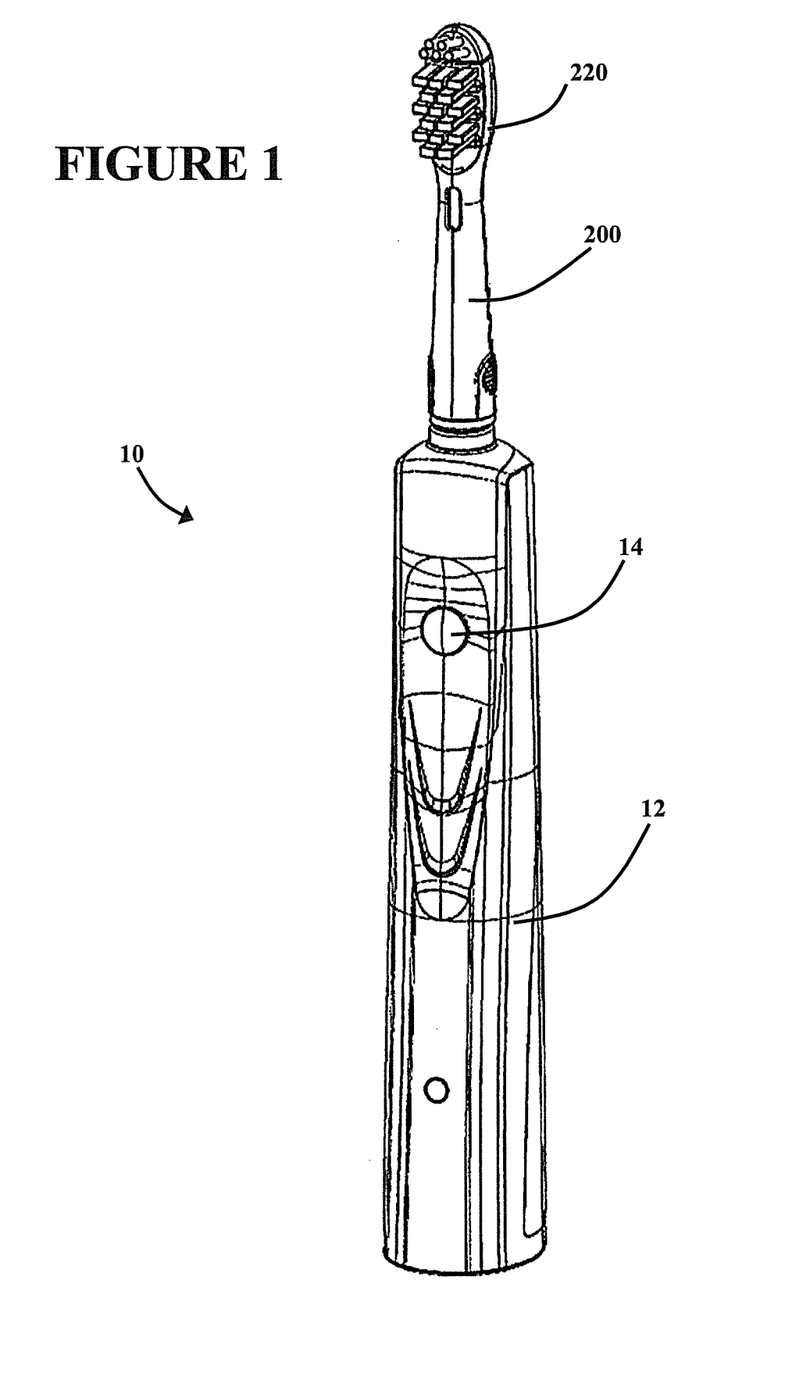
FIG. 1 is a perspective view of an electric toothbrush.

FIG. 1 illustrates an exemplary electric toothbrush 10. The electric toothbrush 10 includes a brush section 200 and a handle section 12. The brush section 200 is more particularly shown in FIGS. 2A to 2E, and is discussed in more detail below. The handle section 12 includes an interior cavity (not shown) which typically contains an electric drive such as a motor, batteries, mechanical linkages for connecting the electric drive to further mechanical linkages in the brush section 200, electronic components for controlling the electrical operation of the toothbrush 10, and the like. In many different embodiments, one or more of those interior components may be omitted, or replaced with other components. For example, a corded electrical power supply can supplant the need for batteries. A switch 14 may be used to turn the electric toothbrush 10 on and off, or otherwise to control operation of the electric toothbrush 10.

The electric drive in the handle section 12 imparts a motion to the mechanical linkages in the handle section 12. It may, for example, impart a rotary, oscillating, or rotary and oscillating motion to the mechanical linkages. The mechanical linkages in the handle section 12 are in turn coupled to additional mechanical linkages in the brush section 200, via a coupling member or the like. A suitable motor and mechanical linkage transmission system is disclosed for example in U.S. Patent Application Publication No. 2008/0307591 to Farrell et al., which is hereby incorporated by reference in its entirety. Movement of the combined mechanical linkages imparts a desired motion to a brush head portion 220 of the brush section 200 such that the brush head portion 220, or any component thereof, is caused to have a desired cleaning motion. Many different kinds of cleaning motions, including rotary, oscillating, vertical and/or horizontal sweeping and the like, may be used. Generally, as used herein, cleaning motion describes any desired or effective movement of the bristles relative to other components in the toothbrush 10 to affect cleaning. Handle sections 12 and mechanical linkages are well known to the skilled artisan. The brush section 200 may be configured for use with such existing handle sections or may be configured with new handle section types, as the case may be.

The brush section 200, shown in more detail by FIGS. 2A to 2E, 3 and 4, may be push-fitted onto the handle section 12. The brush section 200 includes a mounting tube 212 extending along a longitudinal axis 214. The longitudinal axis 214 may coincide with a longitudinal section of a drive shaft member of the mechanical linkages. At a handle end 216, the mounting tube 212 may include a profile ring having an inside contour complementary with an outside contour of the handle section 12. In this manner, the brush section 200 can be push-fitted onto the handle section 12 in a manner preventing relative rotation of the brush section 200 with respect to the handle section 12. A tab/slot, key/spline or other similar structure may be included in the corresponding contour surfaces to facilitate alignment of the brush section 200 with the handle section 12 and to further prevent relative rotation between the two. Alternatively, the mounting tube 212 may be integrally formed with the handle section 12.

The illustrated brush head portion 220 has an elliptical shape, although it may alternatively have a generally rectangular, oblong, or other suitable shape. Generally, the brush head portion 220 may have a length-to-width aspect ratio greater than one, although such an arrangement is not required.

In some embodiments, the brush head portion 220 includes a frame 222 which supports a first plurality of contact elements 224 that are mounted to the frame 222 so as to be fixed, i.e., they are static relative to the frame 222. Any suitable method of mounting the first plurality of contact elements 224 to the frame 222 may be used. For example, where the contact elements 224 comprise a plurality of bristles, methods such as hot tufting, gluing, stapling, and the like, may be utilized. As another example, where the contact elements 224 comprise a plurality of elastomeric elements, methods such as gluing, snap-fitting, welding, molding, etc. may be utilized.

Supported within the frame 222, such as by a snap fit for example, is a movable contact element support or movable contact element holder 226 supporting a second plurality of contact elements 228. The second plurality of contact elements 228 may be mounted to the movable contact element holder 226 using any suitable method, as described above with regard to the first plurality of contact elements 224. The movable contact element holder 226 may be supported within the frame 222 such that it is able to rotate about the longitudinal axis 214 in response to a suitable driving input from the handle section 12, as transferred by the mechanical linkages. In this way the second plurality of contact elements 228 are movable in a cleaning motion relative to the first plurality of contact elements 224.

The first plurality of contact elements 224 may be arranged in rows transverse relative to the axis 214. Similarly, the second plurality of contact elements 228 may be arranged in rows transverse relative to the axis 214. In some embodiments, the transverse rows may alternate between rows of first plurality of contact elements 224 and rows of second plurality of contact elements 228. In some embodiments, multiple rows of the first plurality of contact elements may be separated by a row or multiple rows of the second plurality of contact elements 228 and vice versa or the rows may be interleaved or arranged in virtually any manner. The rows of the first plurality of contact elements 224 may advantageously be longer in length than the rows of the second plurality of contact elements 228.

Figure 2A:
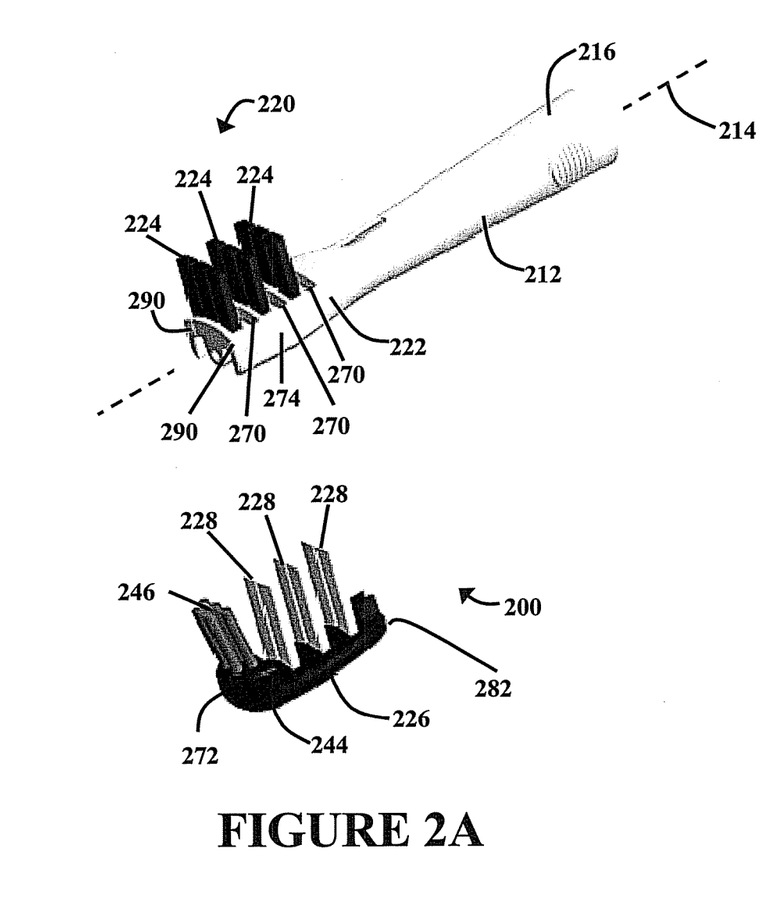
FIG. 2A is an exploded perspective view of the brush section of the toothbrush shown in FIG. 1.
Figure 2B:
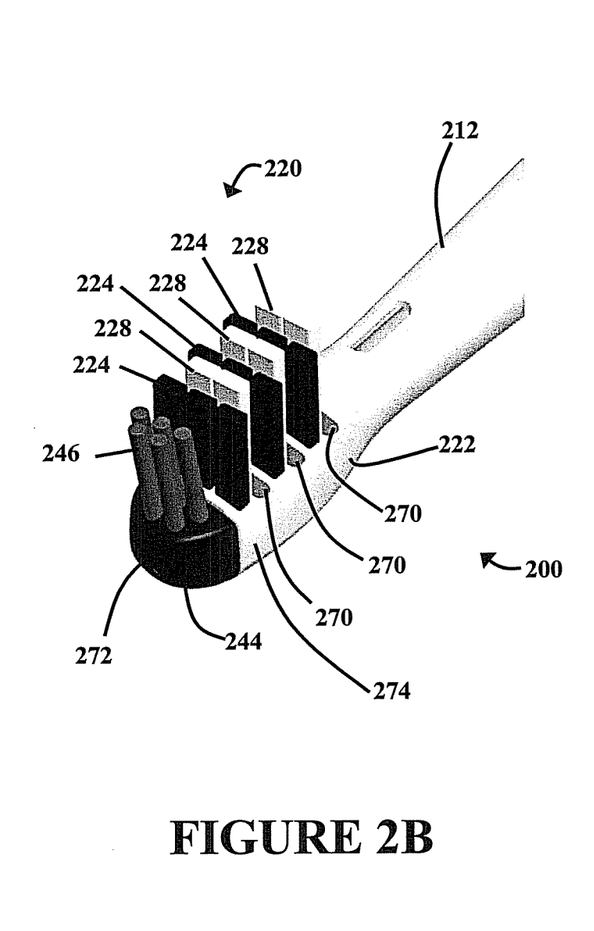
FIG. 2B is a perspective view of the brush section illustrated in FIG. 2A, in an assembled condition.
Figures 2C, 2D:
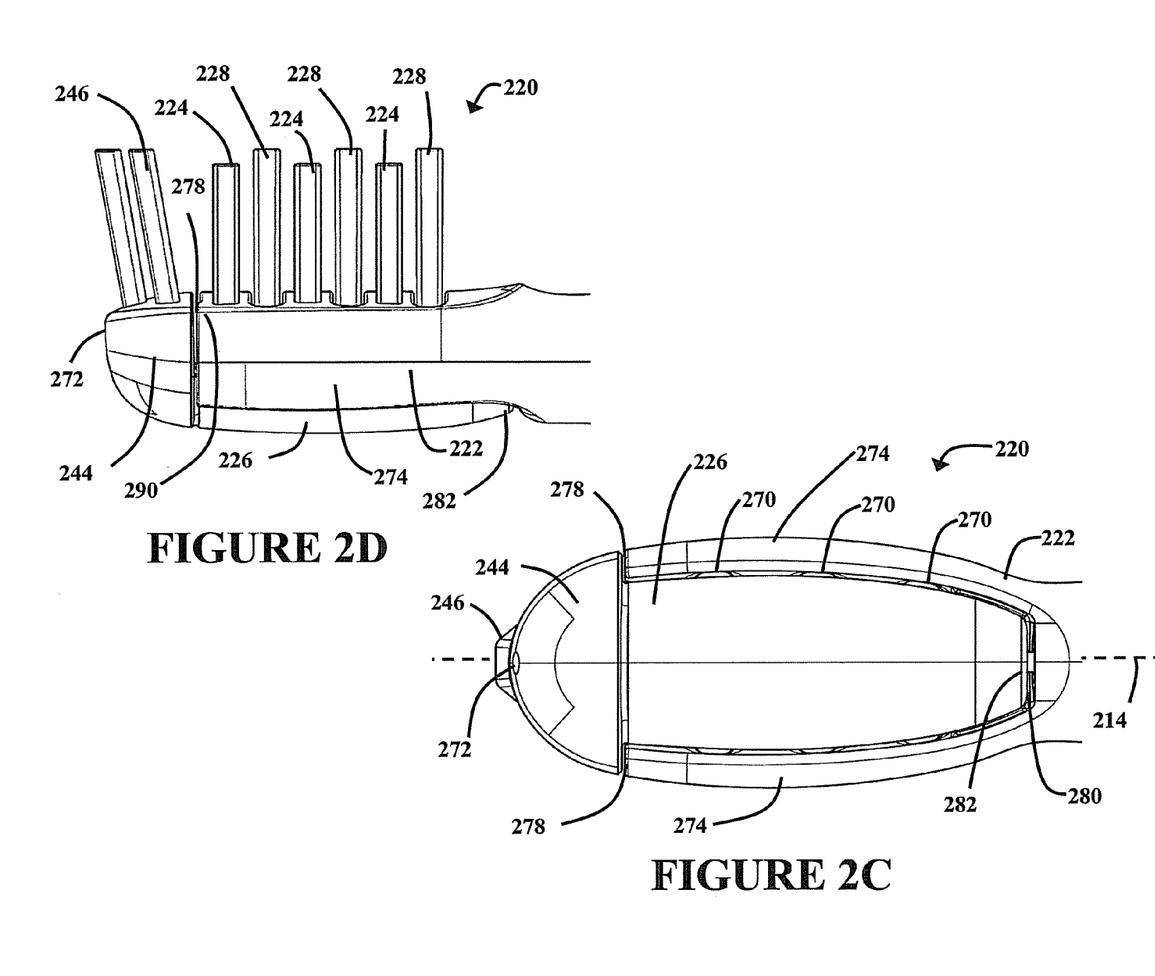
FIG. 2C is a back view of the head portion of the brush section illustrated in FIGS. 2A and 2B.
FIG. 2D is a side view of the head portion of the brush section illustrated in FIGS. 2A to 2C.
Figure 2E:
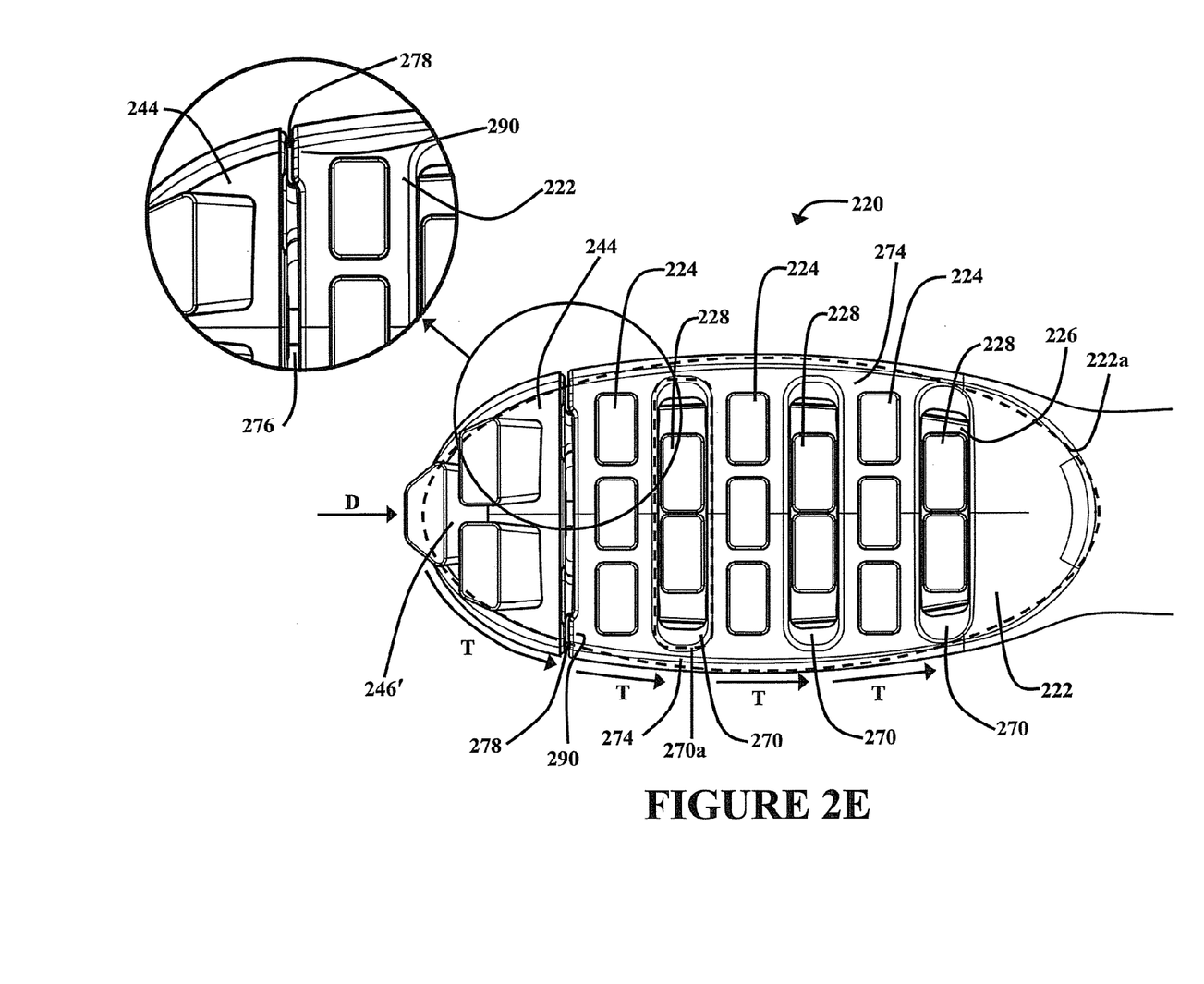
FIG. 2E is a top view of the head portion of the brush section illustrated in FIGS. 2A to 2D, and employing a different bristle configuration at the tip of the head.

The movable contact element holder 226 may include an extension portion 244 supporting a third plurality of contact elements 246. FIG. 2E illustrates a slightly different configuration of contact elements 246' disposed within the extension portion 244 from the other figures herein. The extension portion 244 may be supported to permit at least one freedom of motion relative to the frame 222. For example, the extension portion 244 may be supported to rotate relative to the frame 222. In this manner, the third plurality of contact elements 246 may move in a cleaning motion relative to the first plurality of contact elements 224 and/or the second plurality of contact elements 228. For example, the extension portion 244 may couple to the movable bristle holder 226 such that the third plurality of contact elements 246 moves in a similar manner as the second plurality of contact elements 228.

In the embodiment of FIGS. 2A to 2E, the coupling between the extension portion 244 and the movable contact element holder 226 is direct such that the extension portion 244 moves with the movable contact element holder 226. However, in some embodiments, the extension portion 244 may instead couple to the mechanical linkages in the brush section 200 directly, and/or to the movable contact element holder 226 or otherwise such that the extension portion 244 has a cleaning motion that is separate from a cleaning motion of the movable contact element holder 226 and the second plurality of contact elements 228. In other embodiments, the frame 222 may comprise the extension portion 244 to hold the third plurality of contact elements 246. In such embodiments, the third plurality of contact elements 246 may be stationary with respect to the frame 222.

In the embodiment shown in FIGS. 2A to 2E, the movable contact element holder 226 may oscillate about the axis 214 thereby causing the second plurality of contact elements 228 and/or the third plurality of contact elements 246 to similarly oscillate about the axis 214. The movement of the movable contact element holder 226 may cause the second plurality of contact elements 228 and/or the third plurality of contact elements 246 to oscillate back and forth angularly to provide a cleaning action substantially similar to an up-down manual brushing action. The amount of angular movement as well as the speed exhibited by the movable contact element holder 226 and the second plurality of contact elements 228 and/or the third plurality of contact elements 246 can impact the efficacy of the cleaning action.

In some embodiments, the brush section 200 may comprise a transponder, and the handle section 12 may house a detector or a reading device as described in U.S. Patent Application Publication Nos. 2004/0255409 and 2003/0101526. The transponder can be configured to communicate information about the brush section 200 to the detector or reading device. The reading device or detector can be in signal communication with a controller in the handle section 12 which may be configured to control the speed of the motor and/or the movement of the mechanical linkages in the handle section 12. The basic architecture of a controller, reading device, detector, and/or transponder is generally known.

The speed of the motor as well as the angle of oscillatory shaft displacement can be controlled in any suitable manner. For example, one means of modifying the speed of the motor is to increase or decrease the voltage to the motor. Typically, an increase in voltage will increase the speed of the motor while a decrease in voltage will decrease the speed of the motor. Such mechanisms for modifying the voltage delivered to motors are well known. As another example, the speed of the motor may be modified via a transmission system.

The first plurality of contact elements 224, the second plurality of contact elements 228, and/or the third plurality of contact elements 246 of the present invention may comprise a wide variety of materials and may have a number of different configurations. Any suitable material and/or any suitable configuration may be utilized. For example, in some embodiments, the first plurality of contact elements 224, the second plurality of contact elements 228, and/or the third plurality of contact elements 246, may comprise tufts. The tufts may comprise a plurality of individual filaments which are securely attached to a cleaning element carrier. Such filaments may be polymeric and may include polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 centimeters to about 6 centimeters, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, and a pointed tip. In some embodiments, the filaments may include a dye which indicates wear of the filaments as described in U.S. Pat. No. 4,802,255. Other suitable examples of filaments are described in U.S. Pat. No. 6,018,840. In some embodiments, the cleaning element fields may comprise fins as described in U.S. Pat. No. 6,553,604, and U.S. Patent Application Publication Nos. 2004/0177462; 2005/0235439; and 2005/0060822. In some embodiments, the cleaning element fields may comprise a combination of fins and tufts.

Additionally, at least a portion of some of the first plurality of contact elements 224, the second plurality of contact elements 228, and/or the third plurality of contact elements 246 may be attached to a cleaning element carrier at an angle. Such orientations are described in U.S. Pat. No. 6,308,367. Also, any suitable method may be utilized to attach the first plurality of contact elements 224, the second plurality of contact elements 226, and/or the third plurality of contact elements 246 to their respective structures.

Embodiments are contemplated where the mounting tube 212 is angled with respect to the handle section 12. In such embodiments, the mechanical linkages between the motor and the brush head portion 220 of the present invention may be provided in discrete portions thereby accommodating the angle of the mounting tube 212. For example, the mechanical linkages may include a drive shaft with one or more universal joints, or a drive shaft constructed from a compliant material. Some examples of suitable materials for construction of the drive shaft include aluminum, spring steel, plastics, e.g. delrin, nylon, polypropylene, and/or combinations thereof.

The second plurality of contact elements 228 extend through apertures 270 formed in the frame 222 so that the contact elements 224 and 228 form a unitary contact element field to perform a brushing operation. In operation, the second plurality of contact elements 228 move with respect to the first plurality of contact elements 224, in a motion very similar to the motion a user would perform with a manual oral cleaning device such as a manual toothbrush. A drive shaft (not shown) may extend through the frame 222 to be supported in the extension portion 244 of the movable contact element holder 226. The drive shaft can be adapted to engage a mechanical linkage in the handle section 12. The movable contact element holder 226 is coupled to the drive shaft such that oscillation of the drive shaft causes a like oscillation of the movable contact element holder 226. Alternatively, the movable contact element holder 226 may be coupled by a linkage, cam structure or the like such that the movable contact element holder 226 has a cleaning motion separate from a rotating motion of the drive shaft. The movable contact element holder 226 may be snap-fitted into the frame 222 and engaged with the drive shaft.

As a general matter, electric toothbrush head portions such as the illustrated head portion 220 should be small enough to be inserted into and moved around within a user's mouth. This design goal is complicated by the need to include moving parts in the toothbrush head 220, such as the movable portion 226, each of which must be large enough to adequately hold and retain contact elements such as the contact elements 224, 228 and 246. The various toothbrush head parts also must be sufficiently durable, such as for example to survive a typical drop of the toothbrush. If the toothbrush is dropped, the worst case outcome so far as the head portion is concerned occurs when the tip of the head portion is the part which initially contacts the floor, sink or other surface. In that scenario, the head portion must bear the full weight of the entire toothbrush, including the motor, batteries, and other internal components. Of course, other drop scenarios are also possible, and the head portion should be able to survive any reasonably predictable drop without fracturing or otherwise being materially damaged.

The head portion 220 structure as shown in FIGS. 2A to 2E helps to prevent fracturing or other material damage resulting from impacts to the head portion 220, especially in response to a force D acting on the tip 272 of the head portion 220. Force D, for example, may represent the "dropping force" acting on the toothbrush 10 if it were dropped so that the tip 272 of the head portion 220 is the first part to contact the floor or sink, thus bearing the entire weight of the toothbrush 10. As illustrated in FIG. 2E, such a force D is transmitted T away from the interior region of the head portion 220, and through the two side peripheries 274 of the toothbrush head 220 (the force transmission T being labeled on only one side in the figure). This force transmission is accomplished by the structure of the interface between the extension portion 244 and the frame 222. More particularly, these two components are structured to leave a large gap 276 between them in a central region, and small gaps 278 between them in the side periphery regions 274. In this way, when the extension portion 244 is deflected inwardly by the force D, the first point of contact and therefore force transmission T occurs across the small gaps 278 in the side periphery regions 274. The force transmission T thus travels down the side peripheries 274, around the interior region where the contact elements 224 and 228 are held, and down the tube portion 212 of the brush section 210.

Figure 3:
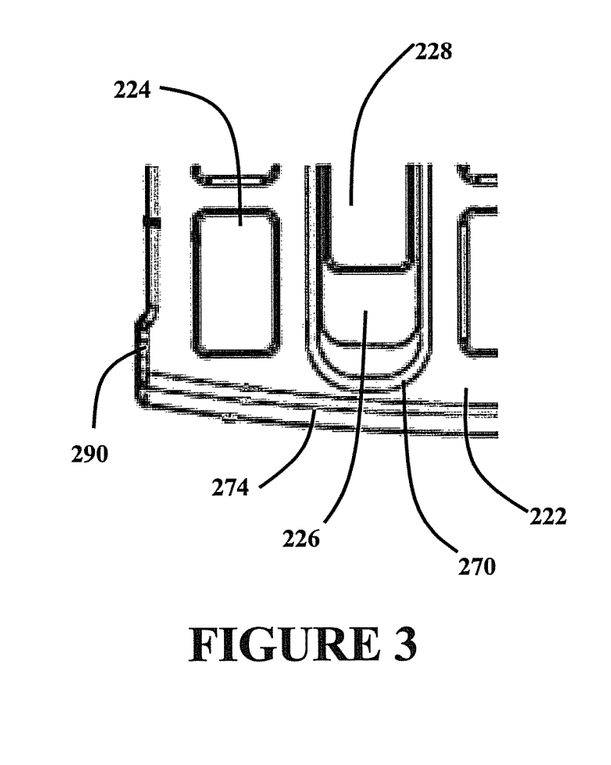
FIG. 3 is a partial top view of the head portion of the brush section illustrated in FIGS. 2A to 2E, focusing on the bumper.
Figure 4:
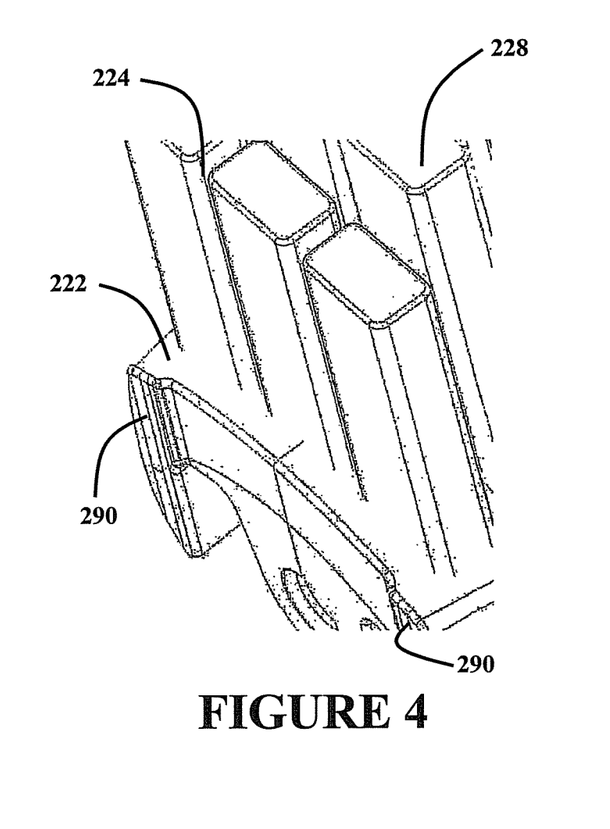
FIG. 4 is a partial perspective view of the head portion of the brush section illustrated in FIGS. 2A to 2E, focusing on the bumper.

In some embodiments, such as the embodiment illustrated in FIGS. 2E, 3 and 4, the small gaps may be formed by bumpers. Thus, the small gaps 278 at the side peripheries 274 are formed in part by frame bumpers 290 extending toward the extension portion 244. Although not illustrated in the figures, the extension portion 244 may also include its own bumpers 292, either alone or in combination with the frame bumpers 290. The illustrated frame bumpers 290 are formed integrally with the material of the frame portion 222. Although not illustrated in the figures, one or the other of the bumpers 290 and 292 may alternatively be formed of a different material. For example, the bumpers 290 and 292 made be made from an elastomeric material having a higher degree of resiliency that the material of the frame portion 222 or the extension portion 244. In that way the resiliency of the bumper material can absorb some of the force transmission T, thus lessening the impact of the force on the entire toothbrush 10 as a whole. Such materials might include, for example, a thermoplastic elastomer (TPE) or any one of several other kinds of materials. One of ordinary skill in the art will be able to determine an appropriate bumper material based on the desired elastic properties, and the requirements for bonding to the frame portion 222 or the extension portion 244 such as by injection molding.

Additional measures may be employed to help transmit the force T more effectively away from the interior region, to travel instead along the side peripheries 274 of the head portion 220. For example, it is advantageous to increase the surface areas of the two surfaces which abut each other across the small gaps 278 as the extension portion 244 is deflected by the force D. This can be accomplished, for example, by making the interface between the extension portion 244 and the frame 222 across the small gaps 278 to be substantially continuous, lacking sharp discontinuities during the rotation cycle of the extension portion 244. When the movable holder 226 is in its neutral state as shown for example in FIGS. 2B and 2E, the interface between the extension portion 244 and the frame 222 is substantially continuous. When the movable holder 226 and the extension portion 244 rotate away from that neutral position, however, the interface will start to become discontinuous and the surface contact area across the gaps 278 decreases. The degree of discontinuity across the small gaps 278 will increase as the holder 226 rotates further away from its neutral position. As one way to reduce this discontinuity, the angular extent of the rotation may be limited. As will be appreciated by one of ordinary skill in the art, this limitation of rotation may be accomplished in many ways, such as by appropriately configuring the coupling between the movable holder 226 and the electric drive in the handle section 12, or by appropriately configuring the fit of the holder 226 into the frame 222, or by other means.

For example, the rotation of the movable contact element holder 226 may be limited so that each of the second plurality of contact elements 228 remain within the vertical envelopes defined by the respective apertures 270 through which the elements 228 extend, such as shown by the dotted curve 270a in FIG. 2E. As an alternative example, the rotation of the movable contact element holder 226 may be limited so that each of the second plurality of contact elements 228 remain within the vertical envelope defined by the outer profile of the head portion 222, such as shown by the dotted curve 222a in FIG. 2E. In yet further embodiments, the rotation may be limited so that only a lower portion of the height of the contact elements 228 above the support structure remains within one or the other of the envelopes 270a, 222a. The lower portion may be, for example, 75 percent, 50 percent, or 25 percent of the height of the contact elements 228.

One of the advantages of directing the force transmission T down the two side peripheries 274 of the head portion 220 is that it protects the interior region of the head portion 220 between the side peripheries 274. The respective interior regions of the frame 222 and the movable contact element holder 226 house the contact elements 224 and 228. Thus the durability of these interior regions can be weakened by bristle staples and the like which hold the contact elements in place. Moreover it may be desirable to pack the elements 224 and 228 in closely together, not only to reduce the overall size of the head 220, but also to form a more effective unitary cleaning surface. A close packing of the elements 224 and 228 may be accomplished by reducing the various wall thicknesses of the frame 222 and contact element holder 226 in the interior region, but that decreases the durability of these parts in that region. Directing the force transmission T down the two side peripheries 274 of the head portion 220 and thus away from the interior region permits a reduced amount of material to be used in the interior region of the head portion 220. This provides a smaller head portion 220 without sacrificing the overall durability of the head portion 220.

Additional measures may be employed to direct the transmission force T away from the interior region of the head portion 220. For example, the gap 280 between the frame 222 and the rear portion 282 of the movable contact element holder 226 may be made small in comparison with the gap 276/278 between the extension portion 244 and the frame 222. In that way, upon application of a force D, a first portion of the force D is absorbed by a bending movement of the extension portion 244 permitted by the relatively large gap 276/278. A second portion of the force D is then transmitted T through the movable portion 226, to be transferred across the rear gap 280 by the rear portion 282 contacting the frame 222 across the rear gap 282. A third portion of the force D can be absorbed by the extension portion 244 eventually closing the front gap 276/278 by contacting the frame 222 across the small gap portions 278. In this regard, the front gap 276/278 may be sufficiently larger than the rear gap 280 so that the third portion of the force D is small enough not to threaten the durability of the interior regions of the brush head 220. In that event, the front gap can take on any desired configuration, such as for example having a substantially uniform width across its entire extent between the two side peripheries 274.

The brush head portion 220 structure can survive drop heights which are normally encountered in a bathroom environment. Such drop heights can range from about 10 centimeters (a typical depth of a sink from its rim to its bottom) to about 70 centimeters or about 80 centimeters (a typical distance between a sink top and the floor). A heavy handle section 12 for the electric toothbrush 10 may weigh on the order of 185 grams, which represents a potential dropping energy of about 1.3 Newtons at a height of 70 centimeters. Thus, in one embodiment, the brush head portion 220 is able to absorb at least about 1.0 Newtons of energy, in another embodiment at least about 1.1 Newtons of energy, in another embodiment at least about 1.2 Newtons of energy, and in yet another embodiment at least about 1.3 Newtons of energy, applied via a force D without fracture or material damage to the brush head portion 220.

It will be understood and appreciated that while various aspects, features and advantages of the invention are described in connection with particular embodiments, the herein described aspects, features and advantages may be implemented in any of the embodiments, and as such, the features and structures of the various embodiments may be mixed and matched yielding a virtually limitless number of combinations. One of skill in the art will furthermore appreciate that the herein described aspects, features and advantages of the invention may be combined with structures and devices known to or later discovered by the skilled artisan.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The preceding text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be combined with or substituted for, in whole or part, any other feature, characteristic, component, composition, ingredient product, step or methodology described herein. Numerous alternative embodiments could be implemented, using either current technology or technology developed after the filing date of this patent, which would still fall within the scope of the claims.

What is claimed is:

1. A brush section for an electrical toothbrush housing an electric drive, the brush section having a head portion comprising:
    a frame including a first plurality of contact elements supported within the frame;
    a movable contact element holder including a second plurality of contact elements supported within the movable contact element holder, the movable contact element holder being structured to receive a cleaning motion from the electric drive to have at least one freedom of motion relative to the first plurality of contact elements;
    an extension portion of the movable contact element holder arranged at a tip end of the head portion, with a gap disposed between the extension portion and the frame; and at least one bumper disposed on at least one of the frame and the extension portion, facing toward the gap;
    wherein at least a first portion of the gap in a side periphery region of the head portion is smaller in width than a second portion of the gap in an interior region of the toothbrush head.

2. The brush section of claim 1, further comprising a third portion of the gap in an opposite side periphery region from the first portion of the gap, wherein the third portion of the gap is smaller in width than the second portion of the gap.

3. The brush section of claim 1, wherein the bumper is composed of a first material, the frame or extension portion on which the bumper is disposed is composed of a second material, and the first material is different from the second material.

4. The brush section of claim 3, wherein the first material is more resilient than the second material.

5. The brush section of claim 1, wherein an interface between the extension portion and the frame across the first portion of the gap is substantially continuous when the movable contact element holder is in a neutral position.

6. The brush section of claim 5, wherein the frame further comprises apertures through which the second plurality of contact elements extend, and movement of the movable contact element holder is limited so that at least a lower seventy-five percent of the height of the second plurality of contact elements remains within vertical envelopes defined by the apertures.

7. The brush section of claim 1, further comprising a rear gap between a rear portion of the movable contact element holder and the frame, wherein the rear gap is smaller in width than the first portion of the gap.

8. A brush section for an electrical toothbrush housing an electric drive, the brush section having a head portion comprising:
    a frame including a first plurality of contact elements supported within the frame;
    a movable contact element holder including a second plurality of contact elements supported within the movable contact element holder, the movable contact element holder being structured to receive a cleaning motion from the electric drive to have at least one freedom of motion relative to the first plurality of contact elements;
    an extension portion of the movable contact element holder arranged at a tip end of the head portion; and
    means for distributing an impact force away from an interior region of the head portion;
    wherein the distribution means further distributes the impact force along a side periphery of the head portion;
    wherein the distribution means comprises a gap disposed between the extension portion and the frame, such that at least a first portion of the gap in a side periphery region of the toothbrush head is smaller in width than a second portion of the gap in an interior region of the toothbrush head;
    and wherein at least one bumper is disposed on at least one of the frame and the extension portion, facing toward the gap.

9. The brush section of claim 8, wherein the head portion further comprises a front gap disposed between the extension portion and the frame, and the distribution means comprises a rear gap between a rear portion of the movable contact element holder and the frame, such that the rear gap is smaller in width than the front gap.

10. The brush section of claim 8, wherein the bumper is composed of a first material, the frame or extension portion on which the bumper is disposed is composed of a second material, and the first material is more resilient than the second material.

11. The brush section of claim 8, wherein the frame further comprises apertures through which the movable contact elements extend, and movement of the movable contact element holder is limited so that at least a lower seventy-five percent of the height of the second plurality of contact elements remains within vertical envelopes defined by the apertures.

12. A brush section for an electrical toothbrush housing an electric drive, the brush section having a head portion comprising:
- a frame including a first plurality of contact elements supported within the frame;
- a movable contact element holder including a second plurality of contact elements supported within the movable contact element holder, the movable contact element holder being structured to receive a cleaning motion from the electric drive;
- an extension portion of the movable contact element holder arranged at a tip end of the head portion, with a gap disposed between the extension portion and the frame; and at least one bumper disposed on at least one of the frame and the extension portion, facing toward the gap;
- wherein the gap is configured such that the brush head portion is able to absorb at least about 1.3 Newtons of energy applied via a force D without fracture.

13. The brush section of claim 12, wherein at least a first portion of the gap in a side periphery region of the head portion is smaller in width than a second portion of the gap in an interior region of the toothbrush head.

* * * * *